(12) United States Patent
Shirai (10) Patent No.: US 10,016,144 B2
(45) Date of Patent: Jul. 10, 2018

(54) BIOLOGICAL SIGNAL ACQUISITION DEVICE AND METHOD FOR ACQUIRING BIOLOGICAL SIGNAL

(71) Applicant: Panasonic Intellectual Property Management Co., Ltd., Osaka (JP)

(72) Inventor: Tetsuya Shirai, Tokyo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 75 days.

(21) Appl. No.: 15/373,122

(22) Filed: Dec. 8, 2016

(65) Prior Publication Data

US 2017/0086699 A1 Mar. 30, 2017

Related U.S. Application Data

(63) Continuation of application No. PCT/JP2015/005543, filed on Nov. 5, 2015.

(30) Foreign Application Priority Data

Feb. 6, 2015 (JP) .................................. 2015-022051

(51) Int. Cl.
*A61B 5/04* (2006.01)
*A61B 5/0408* (2006.01)
(Continued)

(52) U.S. Cl.
CPC ........ *A61B 5/04085* (2013.01); *A61B 5/0428* (2013.01); *A61B 5/0478* (2013.01);
(Continued)

(58) Field of Classification Search
None
See application file for complete search history.

(56) References Cited

U.S. PATENT DOCUMENTS

2005/0187480 A1   8/2005   Kano et al.
2009/0137883 A1   5/2009   Chiba et al.
(Continued)

FOREIGN PATENT DOCUMENTS

JP   2005-237472   9/2005
JP   2009-131321   6/2009
(Continued)

OTHER PUBLICATIONS

International Search Report of PCT application No. PCT/JP2015/005543 dated Jan. 19, 2016.

*Primary Examiner* — Ankit D Tejani
(74) *Attorney, Agent, or Firm* — Renner Otto Boisselle & Sklar, LLP (57) ABSTRACT

A biological signal acquisition device includes an electrode made up of a plurality of cell electrodes, and a controller that acquires an electrical signal from a biological body through a pair of cell electrode groups made up of a part or all of the plurality of cell electrodes. The controller determines a contact condition between the part or all of the plurality of cell electrodes and the biological body, based on a detection signal acquired by scanning the part or all of the plurality of cell electrodes. Further, the controller selects the cell electrodes making up the pair of cell electrode groups, based on the determined contact condition so that contact resistances between the cell electrode groups and the biological body are equal between the pair of cell electrode groups.

13 Claims, 7 Drawing Sheets

(51) Int. Cl.
    *A61B 5/0478*     (2006.01)
    *A61B 5/0492*     (2006.01)
    *A61B 5/0428*     (2006.01)
    *A61B 5/00*     (2006.01)

(52) U.S. Cl.
    CPC .......... *A61B 5/0492* (2013.01); *A61B 5/6843* (2013.01); *A61B 5/7221* (2013.01); *A61B 2562/0209* (2013.01)

(56) References Cited

U.S. PATENT DOCUMENTS

| | | | |
|---|---|---|---|
| 2011/0125002 A1* | 5/2011 | Ershov | A61B 5/0428 600/384 |
| 2011/0306892 A1 | 12/2011 | Kim et al. | |
| 2013/0211478 A1* | 8/2013 | Kelly | A61N 1/3605 607/59 |
| 2014/0343392 A1 | 11/2014 | Yang | |

FOREIGN PATENT DOCUMENTS

| | | |
|---|---|---|
| JP | 2009-219554 | 10/2009 |
| JP | 2011-255187 | 12/2011 |
| WO | 2013/075388 | 5/2013 |

\* cited by examiner

BIOLOGICAL SIGNAL ACQUISITION DEVICE AND METHOD FOR ACQUIRING BIOLOGICAL SIGNAL

BACKGROUND

1. Technical Field

The present disclosure relates to a biological signal acquisition device that acquires a biological signal from a human body or the like, using an electrode.

2. Description of the Related Art

Unexamined Japanese Patent Publication No. 2009-219554 has disclosed a biological signal acquisition device that estimates a contact condition between a human body and an electrode, using a pressure sensor. This electrocardiographic waveform measuring device includes an electrode for measurement made up of an intermediate electrode and a pair of difference electrodes, a biological signal generation unit for generating, as an electrocardiographic signal, a signal indicating a potential difference between the pair of difference electrodes, an estimate unit for estimating an electrostatic capacity between a relevant cell electrode and the human body for each cell electrode making up the electrode for measurement, and a correction unit for correcting an electrocardiographic level of the electrocardiographic signal. This enables an electrocardiographic signal to be obtained, based on reliability in accordance with a contact condition between the electrode and the subject.

SUMMARY

The present disclosure provides a biological signal acquisition device capable of acquiring a favorable biological signal even if a contact condition between an electrode and a biological body is poor.

A biological signal acquisition device in the present disclosure includes an electrode made up of a plurality of cell electrodes, and a controller that acquires an electrical signal from the biological body through a pair of cell electrode groups made up of a part or all of the plurality of cell electrodes. The controller determines a contact condition between the part or all of the plurality of cell electrodes and the biological body, based on a detection signal acquired by scanning the part or all of the plurality of cell electrodes. Further, the controller selects the cell electrodes making up the pair of cell electrode groups so that contact resistances between the cell electrode groups and the biological body are equal between the pair of cell electrode groups, based on the determined contact condition.

Moreover, a method for acquiring a biological signal in the present disclosure is a method in which an electrode made up of a plurality of cell electrodes is brought into contact with a biological body to acquire an electrical signal from the biological body. First, a detection signal is acquired by scanning a part or all of the plurality of cell electrodes. Next, a contact condition between the part or all of the plurality of cell electrodes and the biological body is determined, based on the detection signal. A pair of cell electrode groups is decided from the plurality of cell electrodes, based on the determined contact condition. In the decision of the pair of cell electrode groups, the cell electrodes making up the pair of cell electrode groups are selected so that contact resistances between the cell electrode groups and the biological body are equal between the pair of cell electrode groups. The electrical signal is acquired from the pair of cell electrode groups.

Here, "contact resistances between the cell electrode groups and the human body are equal between the pair of cell electrode groups" is not limited to "contact resistances between the cell electrode groups and the human body completely coincide with each other between the pair of cell electrode groups", but includes a range where the contact resistances are approximate enough to acquire the biological signal even though the contact resistances do not completely coincide with each other.

The biological signal acquisition device and the method for acquiring the biological signal in the present disclosure are effective in acquiring the favorable biological signal even if the contact condition between the electrode and the biological body is poor.

DETAILED DESCRIPTION

Hereinafter, with reference to the drawings as needed, exemplary embodiments will be described in detail. However, more detailed description than necessary may be omitted. For example, detailed description of a well-known item or redundant description of substantially the same configuration may be omitted. This is to avoid unnecessary prolixity of the following description, and to facilitate understanding of those skilled in the art.

The accompanying drawings and the following description are provided for those skilled in the art to sufficiently understand the present disclosure, and are not intended to limit the subject matters of the claims.

First Exemplary Embodiment

Hereinafter, with reference to FIGS. 1 to 3, a first exemplary embodiment will be described.

Since biological signals of an electrocardiogram, an electromyogram, an electroencephalogram, and the like are weak (several mV), a differential amplifier is used as amplifier 113 when those biological signals are acquired. The differential amplifier includes two input terminals as differential input terminals, and one output terminal. The differential amplifier amplifies a difference of an input signal between the differential input terminals to output the resultant. The use of the differential amplifier can remove noise having the same phase appearing in the differential input terminals (hereinafter, referred to as common mode noise).

Thus mixture of external noise such as hum noise is suppressed. For removing the common mode noise, differential signal paths from a human body to the differential input terminals of the differential amplifier are required to be electrically symmetrical between differential lines. If the differential signal paths are electrically asymmetrical between the differential lines, the common mode noise is not completely removed, and is mixed in the acquired biological signal. Accordingly, it is desirable that contact resistances between the human body and differential electrodes, wiring resistances from the differential electrodes to the differential amplifier are equal between the differential lines.

[1-1. Configuration]

[1-1-1. Configuration of Biological Signal Acquisition Device]

Figure 1:
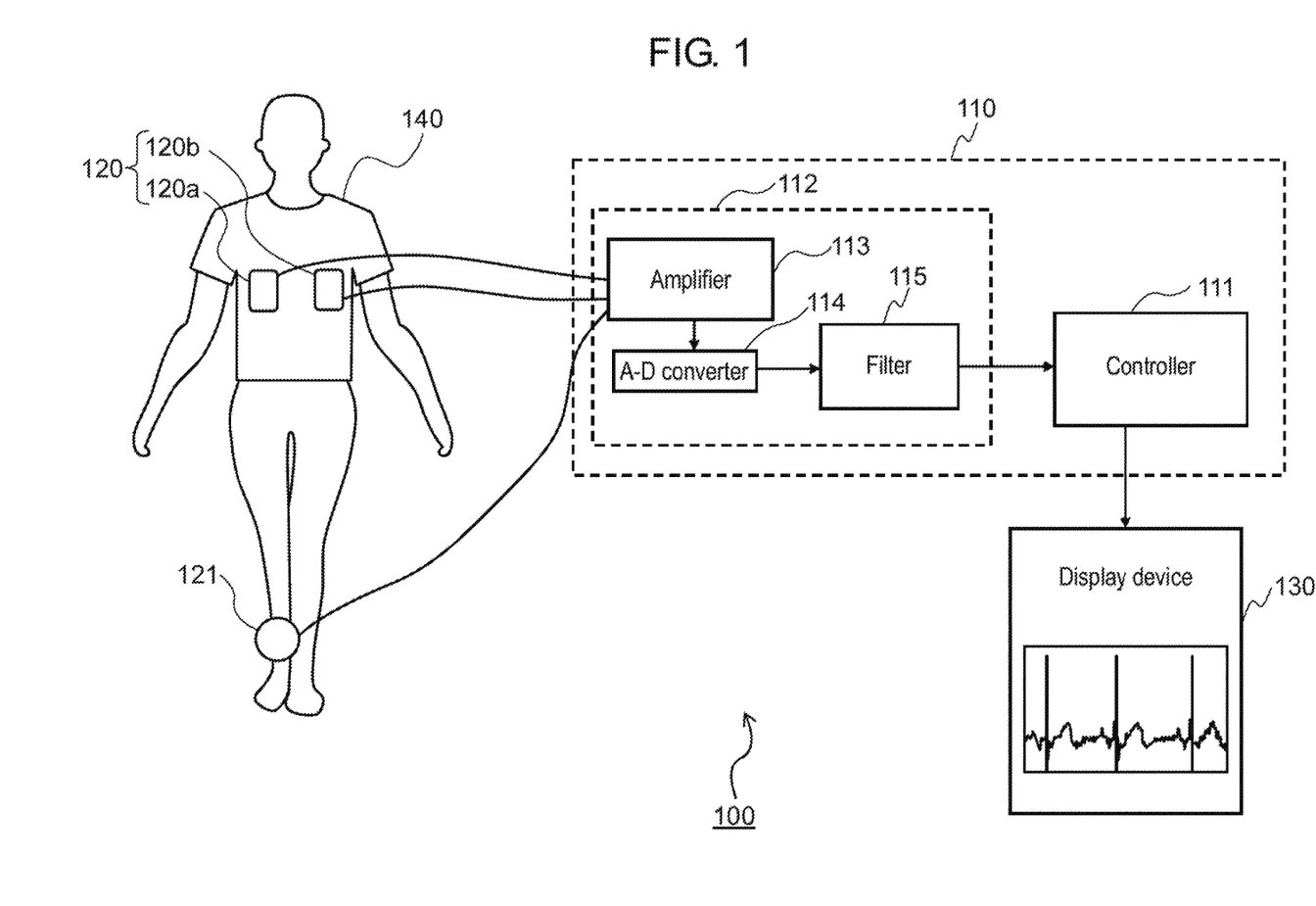
FIG. 1 is a schematic view for describing a biological signal acquisition device in a first exemplary embodiment.

FIG. 1 is a schematic view for describing biological signal acquisition device 100. Biological signal acquisition device 100 includes electrode 120 made up of R electrode 120a and L electrode 120b, reference electrode 121, electrocardiograph 110, and display device 130.

Electrode 120 is an electrode to be brought into direct contact with the human body. In electrode 120, a contact portion with the human body only needs to be made of a conductive material. Electrode 120 is configured by using conductive fibers excellent in flexibility to adhere to the human body. Moreover, an area of electrode 120 is desirably larger to lower the contact resistance between the human body and electrode 120. Electrode 120 is made up of R electrode 120a and L electrode 120b, which are a pair of differential electrodes. When an electrocardiogram is acquired, R electrode 120a and L electrode 120b are disposed so as to sandwich a heart. The electrocardiogram can be acquired by measuring potential differences between R electrode 120a and reference electrode 121 and between L electrode 120b and reference electrode 121. Reference electrode 121 is not limited to a position shown in FIG. 1, but may be disposed at another position where an electrocardiographic waveform can be acquired. Moreover, a contact area of reference electrode 121 is desirably larger to lower the contact resistance. It is also possible to acquire an electrocardiogram from a potential difference between R electrode 120a and L electrode 120b, so that reference electrode 121 is not essential.

Electrocardiograph 110 is made up of signal amplifier 112 to amplify a weak biological signal, and controller 111 that performs control of biological signal acquisition device 100 and various types of signal processing. Electrocardiograph 110 measures a weak electrical signal that occurs in the human body to acquire the biological signal. Signal amplifier 112 includes, as amplifier 113, a differential amplifier with R electrode 120a and L electrode 120b as differential input terminals. Moreover, signal amplifier 112 includes A-D converter 114 to perform A-D conversion (analog-digital conversion) on the electrical signal acquired from R electrode 120a and L electrode 120b and output the resultant to controller 111. Controller 111 processes the acquired electrical signal to obtain the biological signal (the electrocardiographic waveform or the like). The controller 111 may have A-D converter 114 built therein, and signal amplifier 112 may not include A-D converter 114. Signal amplifier 112 and controller 111 includes filter 115 such as a low-pass filter and the like. An analog filter may be used as filter 115, and filter 115 may be disposed between amplifier 113 and A-D converter 114. Moreover, when a digital filter is used as filter 115, signal amplifier 112 may not include filter 115, and only controller 111 may include filter 115. Controller 111 is configured, for example, by a microcontroller.

Display device 130 is a device that visually displays the biological signal received from electrocardiograph 110 as a waveform. As display device 130, a display terminal such as a PC (personal computer) and a smartphone can be used.

Figure 2:
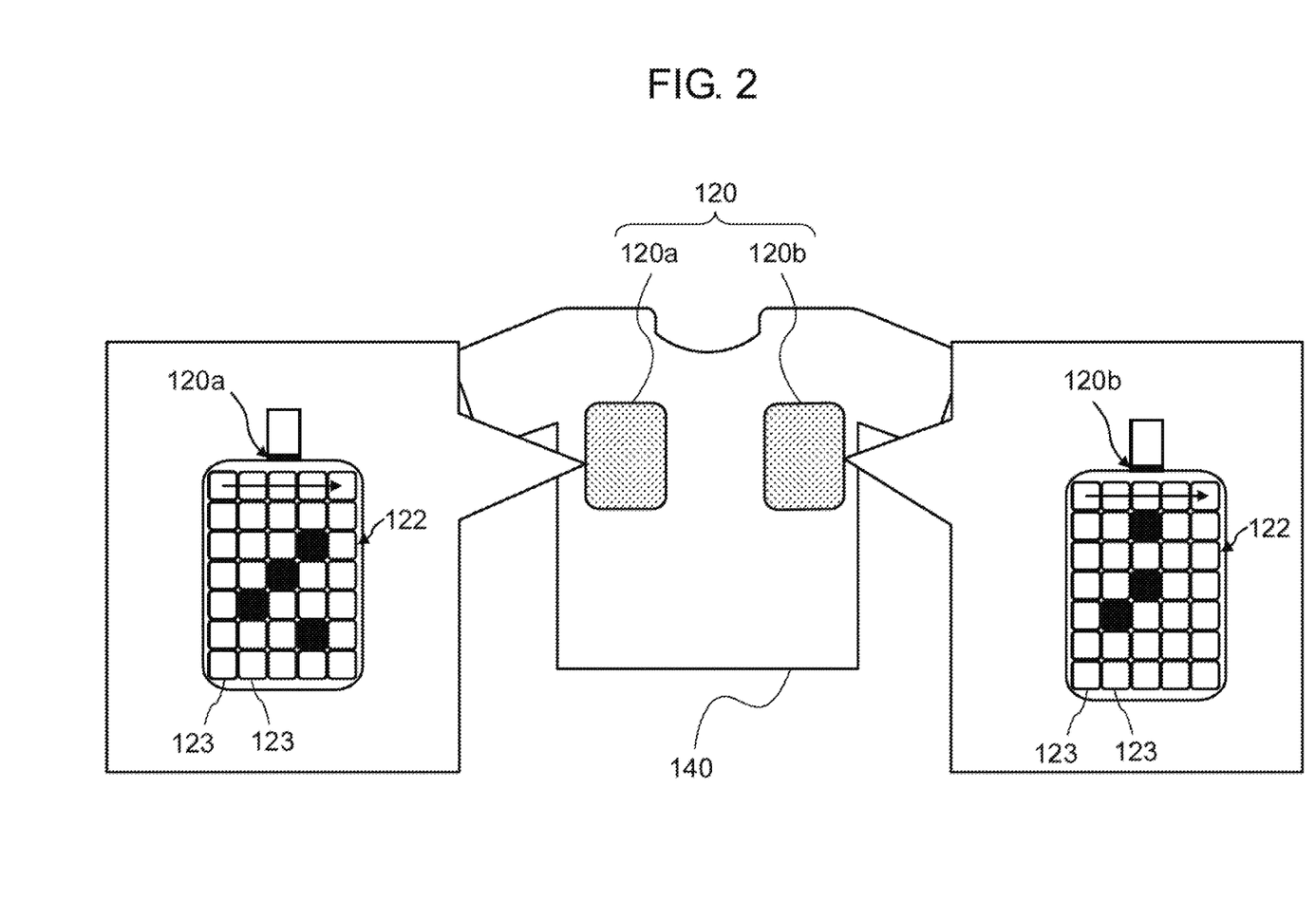
FIG. 2 is a schematic view showing a configuration of an electrode in the first exemplary embodiment.

FIG. 2 is a view for describing electrode 120.

Electrode 120 includes R electrode 120a and L electrode 120b. R electrode 120a and L electrode 120b are each divided into at least two or more cell electrodes 123. For example, as shown in FIG. 2, R electrode 120a and L electrode 120b are each divided into a matrix form. Cell electrodes 123, each of which is a minimum unit forming the matrix, can individually acquire a detection signal. Cell electrodes 123 may have the same size, or may have different sizes, depending on positions of cell electrodes 123. Moreover, arrangement of cell electrodes 123 may not be uniform.

The configuration that enables the detection signal to be acquired individually from each of cell electrodes 123 can be realized, for example, by providing a switch controlled by controller 111 between each of cell electrodes 123 and amplifier 113. In this configuration, it is desirable that the detection signal from single cell electrode 123 is amplified, using amplifier 113 as the differential amplifier. Consequently, in amplifier 113, one input terminal of the differential input terminals is connected to any of cell electrodes 123, and the other input terminal is connected to a steady voltage. Fixing one of the differential input terminals allows the detection signal from single cell electrode 123 to be amplified, using amplifier 113 as the differential amplifier. Thereby, the detection signal from each of cell electrodes 123 can be acquired individually without providing a new amplifier in addition to amplifier 113.

Electrode 120 is attached to T shirt 140. A user wears T shirt 140 to thereby bring the human body into contact with electrode 120 and to acquire the electrocardiographic waveform.

[1-2. Operation]

Hereinafter, operation of biological signal acquisition device 100 having cell electrodes 123 and configured as described above will be described with reference to FIG. 3.

Figure 3:
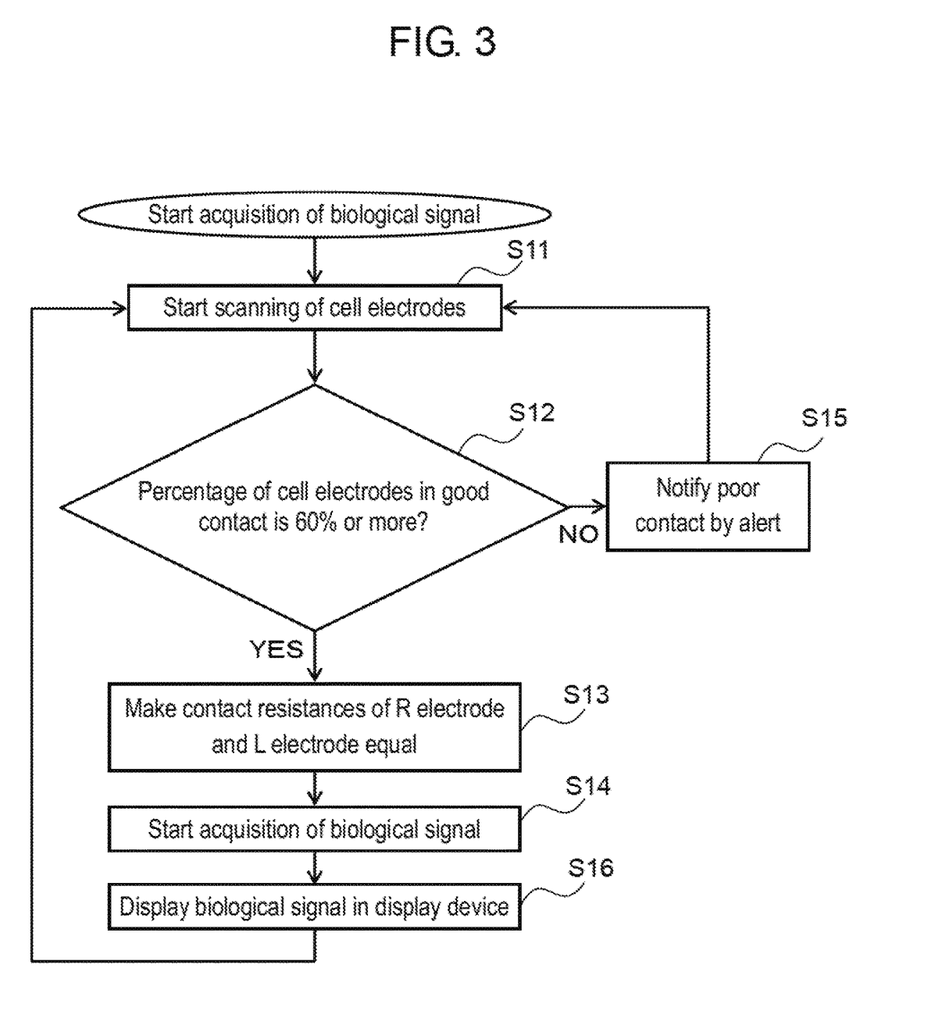
FIG. 3 is a flowchart for describing acquisition operation of a biological signal of the biological signal acquisition device in the first exemplary embodiment.

FIG. 3 is a flowchart for describing operation according to biological signal acquisition in biological signal acquisition device 100 including cell electrodes 123.

[1-2.1. Contact Condition Determination of Each Cell Electrode]

First, controller 111 determines whether or not each of cell electrodes 123 of electrode 120 is in good contact with the human body, based on the waveform of the acquired detection signal. If foreign substances or air is caught between cell electrode 123 and the human body, thereby bringing about a poor contact condition, large noise is mixed in the detection signal acquired from relevant cell electrode 123. That is, the contact condition between cell electrode 123 and the human body can be determined, based on an amount of noise included in the detection signal. For example, based on whether or not the amount of noise included in the detection signal exceeds an arbitrary threshold, the contact condition between cell electrode 123 and the human body is determined.

The determination of the contact condition can be performed, based on a component other than the noise included in the detection signal. For example, controller 111 may apply a test signal between arbitrary electrodes, and the contact condition may be determined, based on a test signal component included in the detection signal acquired in cell electrode 123 as an object of the determination. Moreover, the test signal may be an alternating current, or may be a direct current. For a pair of electrodes to which the test signal is applied, one or more cell electrodes 123 are selected from R electrodes 120a as one, and one or more cell electrodes 123 are selected from L electrode 120b as the other, which makes the determination of the contact condition easy. As the electrode to which the test signal is applied, reference electrode 121 may be used.

The determination of the contact condition can also be performed, based on, for example, a component included in the detection signal and attributed to the biological signal. Cell electrode 123 whose detection signal hardly includes the component attributed to the biological signal can be determined to be in a poor contact condition with the human body.

In step S11, controller 111 starts scanning of cell electrodes 123 to acquire the detection signal from each of cell electrodes 123, by which the contact condition of each of cell electrodes 123 is determined. Controller 111 counts the number of cell electrodes 123 in a good contact condition, based on the determined contact condition. For this, the number of cell electrodes 123 in good contact may be counted in order from a better contact condition, or on the contrary, the number of cell electrodes 123 in poor contact may be counted.

Next, controller 111 determines whether or not a percentage of the number of cell electrodes 123 in good contact with the human body is 60% or more for each of R electrode 120a and L electrode 120b (S12). If the percentage is 60% or more (in the case of "YES" in S12), the processing advances to step S13. Here, while the percentage of the number of cell electrodes 123 in good contact is set to 60%, the present exemplary embodiment is not limited to this percentage because a percentage at which a favorable electrocardiographic waveform can be obtained differs, depending on a resistance value of a material used for cell electrodes 123, and the like.

In step S13, a pair of cell electrode groups 122 is selected from R electrode 120a and L electrode 120b so that contact resistances between respective cell electrode groups 122 and the human body become equal. Of cell electrodes 123 making up R electrode 120a and L electrode 120b, cell electrodes 123 included in the pair of cell electrode groups 122 are connected to signal amplifier 112, while cell electrodes 123 not included in the pair of cell electrode groups 122 are put into an open-circuit condition. This makes the contact resistance between R electrode 120a and the human body equal to the contact resistance between L electrode 120b and the human body. Here, "equal" only needs to mean that the contact resistances are sufficiently approximate in acquisition of the biological signal, and does not necessarily mean that the contact resistances strictly coincide with each other. The same applies in the following description.

The selection of cell electrode groups 122 in step S13 will be described.

First, a pair of candidate groups is selected from R electrode 120a and L electrode 120b. Of cell electrodes 123 of R electrode 120a, cell electrodes 123 in poor contact with the human body are each put into an open-circuit condition, and remaining cell electrodes 123 are set as one of the candidate groups. Similarly, for L electrode 120b, cell electrodes 123 in poor contact with the human body are each put into an open-circuit condition, and remaining cell electrodes 123 are set as the other candidate group.

Next, the pair of respective cell electrode groups 122 is selected from the pair of corresponding candidate groups. The pair of cell electrode groups 122 is selected so that the contact resistances between respective cell electrode groups 122 and the human body are equal. For example, contact areas between cell electrode groups 122 and the human body may be made equal. As the method for making the contact areas between cell electrode groups 122 and the human body equal, when cell electrodes 123 are same size, the numbers of cell electrodes 123 in respective cell electrode groups 122 are desirably equal. Here, since the numbers of cell electrodes 123 are equal between the pair of cell electrode groups 122, cell electrodes 123 in the good contact condition may be put into the open-circuit condition. When the sizes of respective cell electrodes 123 are different, cell electrodes 123 only need to be selected so that the contact areas are equal without depending on the numbers of cell electrodes 123. Thereby, the pair of cell electrode groups 122 that makes the contact resistances with the human body equal can be selected from the pair of candidate groups.

As a method for selecting cell electrode groups 122 so that the contact resistances between the pair of cell electrode groups 122 and the human body are equal, another method may be used. For example, a voltage may be applied to the pair of cell electrode groups 122 to thereby estimate a difference between the contact resistances. Alternatively, in the scanning in step S11, the contact resistance of each of cell electrodes 123 may be estimated, and cell electrode groups 122 may be selected, based on the estimated contact resistances.

After the contact resistances of R electrode 120a and L electrode 120b with the human body are made equal in step S13, electrocardiograph 110 starts the acquisition of the biological signal in step S14.

On the other hand, if the percentage of the electrodes in the good contact condition is less than 60% in step S12 (in the case of "NO" in S12), the poor contact is notified to the user by an alert in display device 130 to promote improvement of the contact condition (S15).

In step S14, information of the acquired biological signal may be displayed in display device 130 (S16), or may be accumulated in a memory (not shown).

The operation from steps S11 to S13 can be carried out by arbitrary operation by the user. The operation can also be set so as to be carried out every arbitrary period. Alternatively, the operation can also be carried out when the contact condition between electrode 120 and the human body changes. The change of the contact condition can be sensed by change of the electrical signal acquired from electrode 120. Also, the change of the contact condition can be sensed by an acceleration sensor or the like (not shown).

[1-3. Effects and the Like]

As described above, the right and left electrodes are each divided into the plurality of cell electrodes to form the pair of cell electrode groups, using the cell electrodes in the good contact condition. The biological signal is acquired through this pair of cell electrode groups, by which the favorable biological signal can be acquired and the electrocardiographic waveform having less noise can be generated.

This enables the favorable biological signal to be acquired even if the contact condition between the electrode and the human body is poor.

Moreover, since biological signal acquisition device 100 according to the present exemplary embodiment selects the pair of cell electrode groups after determining the contact condition of the cell electrodes, the favorable biological signal can be acquired even if attachment conditions of R electrode 120a and L electrode 120b are slightly varied. This makes it unnecessary for the user to finely adjust a position of electrode 120, which can reduce a burden of positioning of electrode 120.

Second Exemplary Embodiment

[2-1. Configuration]

With reference to FIGS. 4 to 7, biological signal acquisition device 100 according to a second exemplary embodiment will be described. Components similar to those in the first exemplary embodiment are given the same reference numerals, and description of configurations and functions similar to those in the first exemplary embodiment may be omitted.

Figure 4:
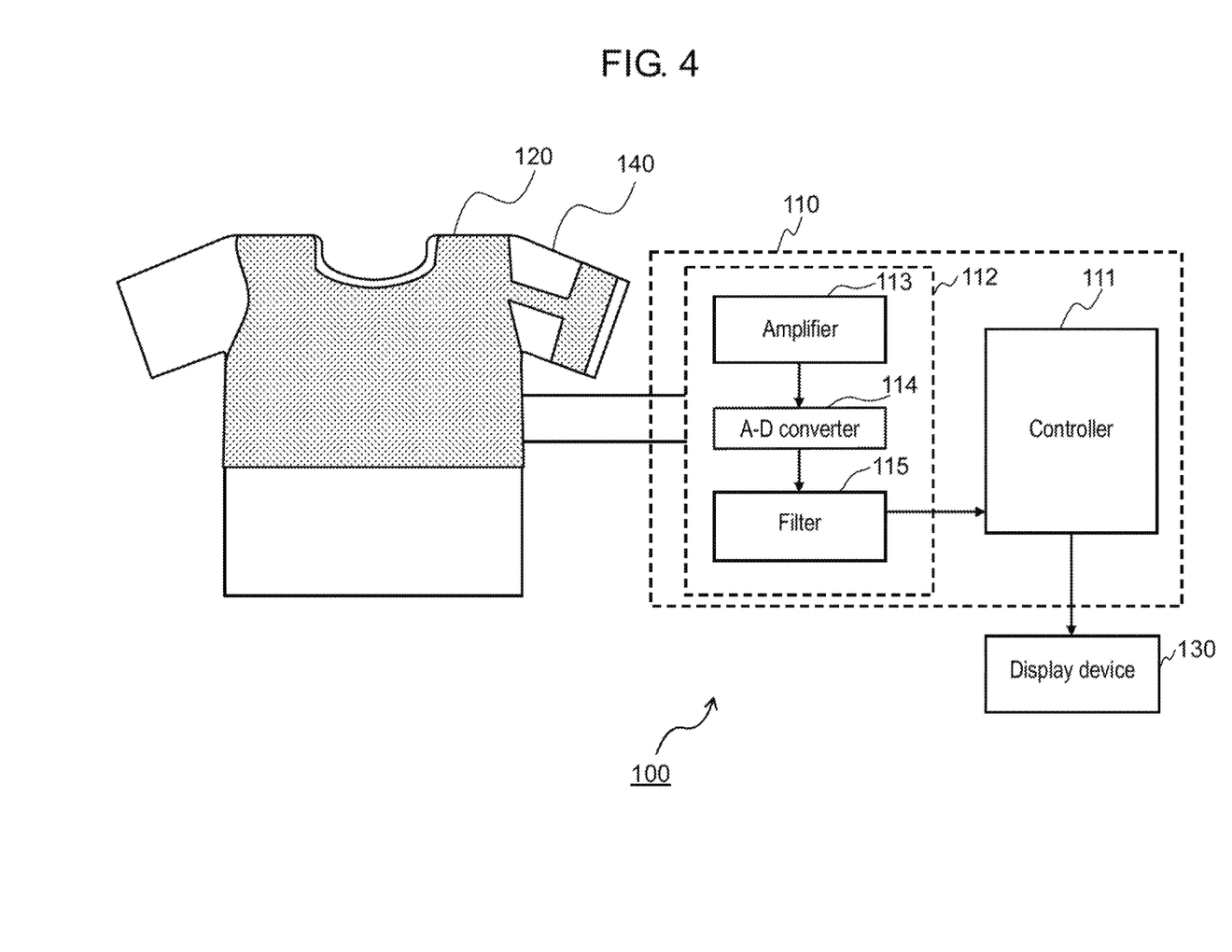
FIG. 4 is a schematic view showing a configuration of a biological signal acquisition device in a second exemplary embodiment.

Electrode 120 of biological signal acquisition device 100 according to the second exemplary embodiment is not divided into R electrode 120a and L electrode 120b as in electrode 120 of the first exemplary embodiment. Electrode 120 is disposed so as to cover whole T shirt 140 or to such an extent as to cover a torso of a human body. In electrode 120, cell electrodes 123, each of which is a minimum unit of the electrode, are arranged in a matrix.

Figure 6:
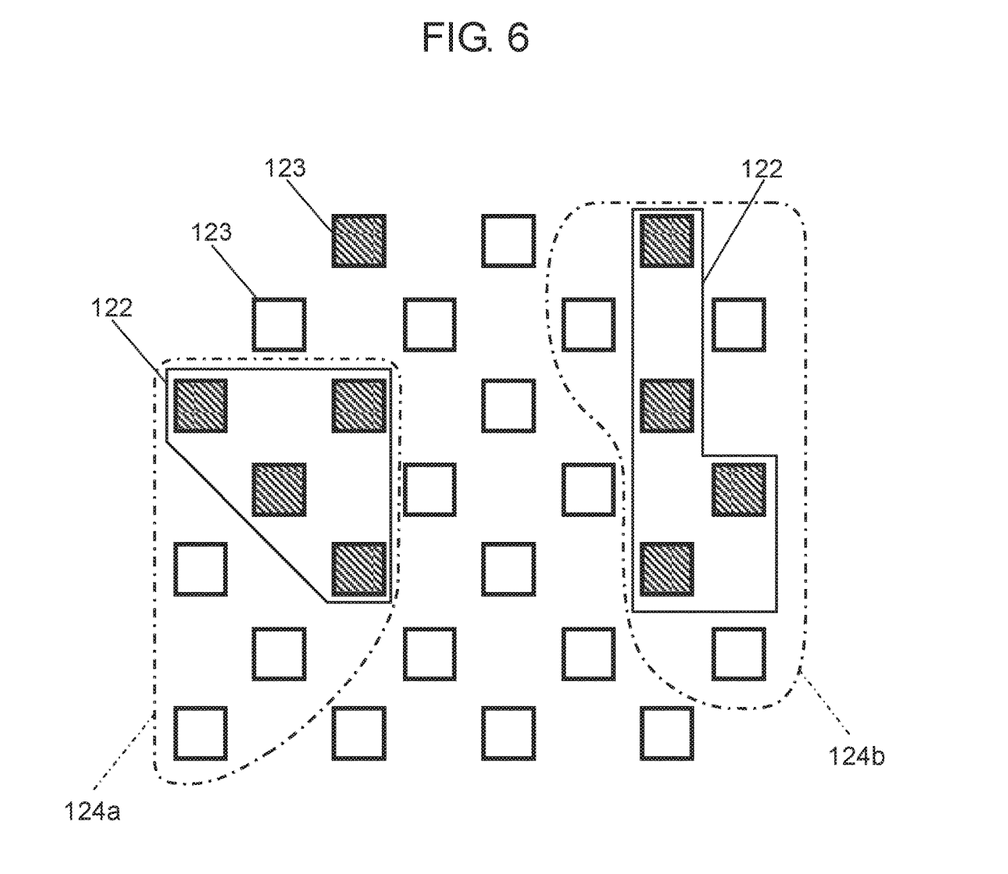
FIG. 6 is a schematic view for describing decision processing of cell electrode groups in the second exemplary embodiment.

Electrode 120 according to the second exemplary embodiment may be disposed in an upper half of T shirt 140. Moreover, as the arrangement in matrix, cell electrodes 123 may be, for example, aligned diagonally, as shown in FIG. 6.

A pair of cell electrode groups 122 can be arbitrarily selected from cell electrodes 123 making up electrode 120. Cell electrodes 123 included in the pair of cell electrode groups 122 are connected to respective terminals on corresponding sides of differential input terminals of amplifier 113. Cell electrodes 123 not included in the pair of cell electrode groups 122 are each put into an open-circuit condition, and are not connected to the differential input terminals of amplifier 113.

[2-2. Operation]

Next, with reference to FIG. 5, operation of biological signal acquisition device 100 according to the second exemplary embodiment will be described. A description will be given, focusing on different points from the first exemplary embodiment, and description of similar points may be omitted.

Figure 5:
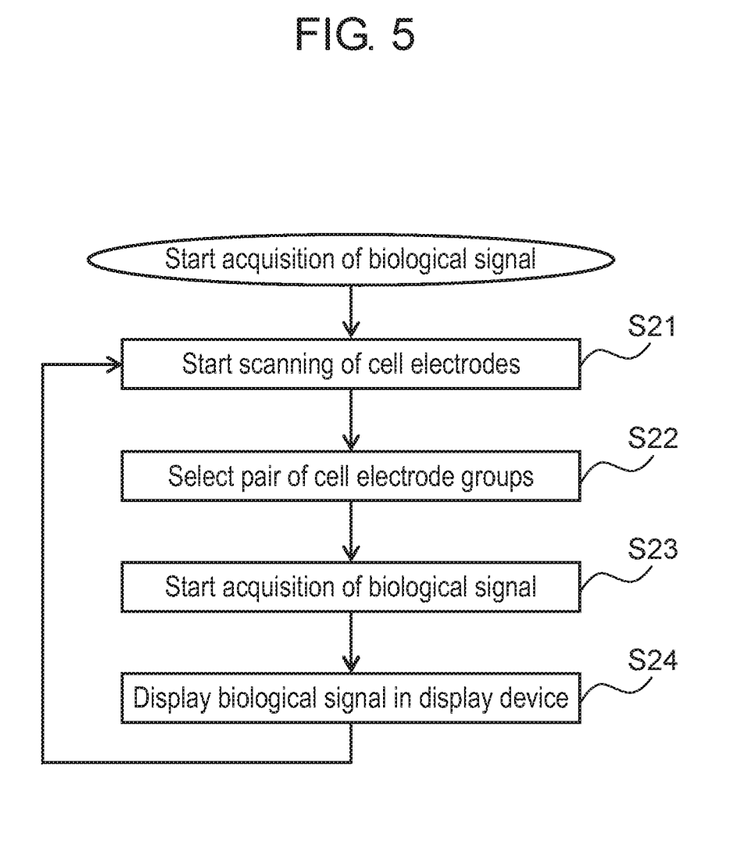
FIG. 5 is a flowchart for describing acquisition operation of a biological signal of the biological signal acquisition device in the second exemplary embodiment.

FIG. 5 is a flowchart for describing biological signal acquisition operation in biological signal acquisition device 100 including cell electrodes 123.

First, controller 111 starts scanning of cell electrodes 123. That is, a detection signal is acquired from each of cell electrodes 123 to determine a contact condition between the human body and each of cell electrodes 123 (S21). Here, cell electrodes 123 in a good contact condition may be determined, or cell electrodes 123 in a poor contact condition may be determined.

Next, controller 111 decides a pair of cell electrode groups 122 used for acquisition of a biological signal (S22). These cell electrode groups 122 are aggregations of cell electrodes 123. The cell electrode groups 122 are disposed on the opposite side of the heart. However, cell electrodes 123 included in neither of the pair of cell electrode groups 122 may be interposed between the pair of cell electrode groups 122. Here, cell electrodes 123 used as cell electrode groups 122 are selected sequentially from cell electrodes 123 in the good contact condition with the human body. The contact condition between each of cell electrodes 123 and the human body is determined, based on a voltage waveform of the detection signal acquired from relevant cell electrode 123. Moreover, the selection is made so that the numbers of cell electrodes 123 used in respective cell electrode groups 122 become equal between the pair of cell electrode groups 122.

Next, the acquisition of the biological signal is started, using two cell electrode groups 122 decided in step S22 (S23).

Information of the biological signal acquired in step S23 can be displayed in display device 130 (S24), or can be accumulated in a memory not shown.

Steps S21 and S22 may be started by a switch (not shown), or may be repeatedly started every preset period.

Figure 7:
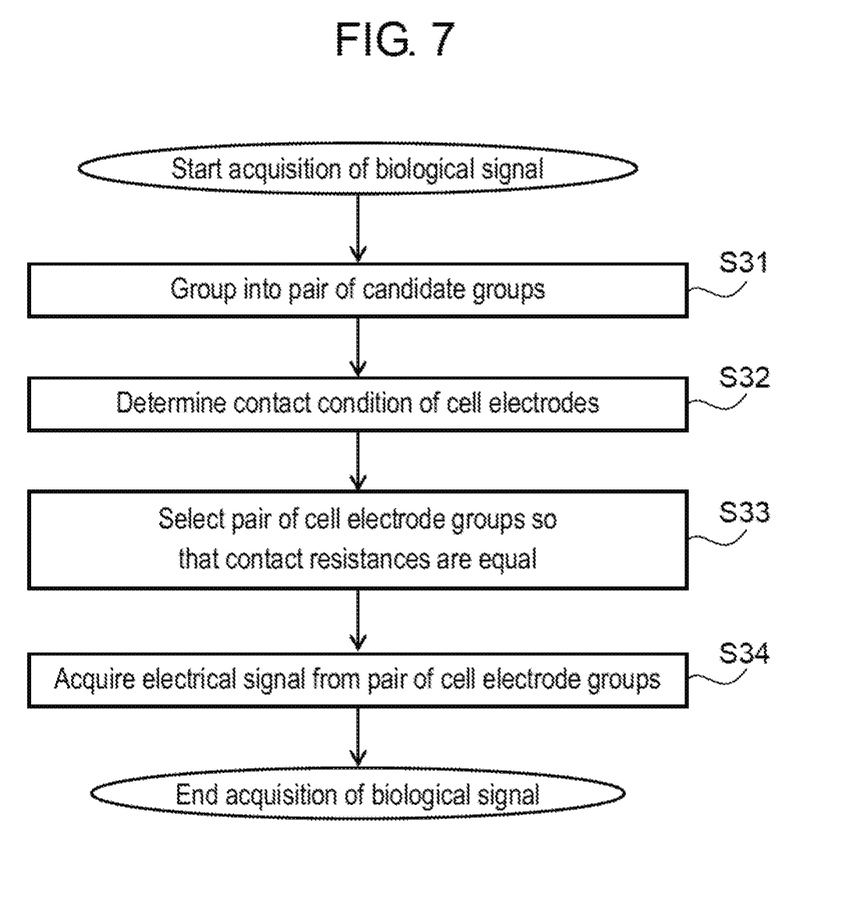
FIG. 7 is a flowchart for describing the decision processing of the cell electrode groups in the second exemplary embodiment.

FIG. 6 is a view for describing details of step S22. FIG. 7 is a flowchart showing the details of step S22.

In step S31 in FIG. 7, cell electrodes 123 making up electrode 120 included in biological signal acquisition device 100 are grouped into candidate group 124a and candidate group 124b. Of cell electrodes 123 making up electrode 120, there may be cell electrodes 123 included in neither of candidate group 124a and candidate group 124b. In step S31, candidate group 124a and candidate group 124b may not be grouped so that contact resistances between the respective candidate groups and the human body are equal. As a method for selecting cell electrodes 123 making up candidate group 124a and candidate group 124b, for example, the selection may be made from combinations of a plurality of cell electrodes 123 decided beforehand. At this time, for each of the combinations of candidate group 124a and candidate group 124b, an intensity of a differential signal component of an electrical signal acquired from the relevant combination may be determined to select the combination having a larger intensity of the differential signal component.

In step S32, the contact condition of each of cell electrodes 123 is determined, based on the detection signal acquired by scanning each of cell electrodes 123. Cell electrode 123 in the poor contact condition may be excluded from candidate group 124a and candidate group 124b selected in step S31.

In step S33, the pair of cell electrode groups 122 is selected so that one cell electrode group 122 is selected from candidate group 124a, other cell electrode group 122 is selected from candidate group 124b, and the contact resistances are equal.

In step S34, only cell electrodes 123 included in the pair of cell electrode groups 122 are connected to the respective differential input terminals of amplifier 113, and controller 111 can acquire an electrical signal from the human body.

[2-3. Effects and the Like]

In biological signal acquisition device 100 configured as described above, controller 111 selects cell electrode groups 122 used for the acquisition of the biological signal, based on the contact condition between each of cell electrodes 123 and the human body. This enables the favorable biological signal to be acquired, even if the contact condition between the electrode and the human body is poor.

Moreover, since the pair of cell electrode groups is selected after the contact condition of each of the cell electrodes is determined, the favorable biological signal can be acquired, even if a contact position slightly varies, depending on a wearer of T shirt 140. This makes it unnecessary for the user to finely adjust a position of electrode 120, which can reduce a burden of positioning of electrode 120. For example, the user can automatically obtain an optimal electrocardiographic waveform without positioning electrode 120.

Other Exemplary Embodiments

As described above, the first and second exemplary embodiments have been described as illustrations of the technique disclosed in the present application. However, the technique in the present disclosure is not limited thereto, and can also be applied to exemplary embodiments resulting from making modifications, replacements, additions, omissions, and the like. Moreover, the respective components described in the foregoing first and second exemplary embodiments can be combined to obtain a new exemplary embodiment.

Consequently, other exemplary embodiments will be exemplified below.

In the first and second exemplary embodiments, the description has been given, using T shirt 140 as an example of a mounting fixture that mounts electrode 120. As this mounting fixture, any mounting fixture that brings electrode 120 into contact with the human body may be employed. Accordingly, the mounting fixture is not limited to the T shirt.

Moreover, biological signal acquisition device 100 is not limited to a device that acquires the biological signal from the human body, and may be a device using a biological body other than a human being as an object.

In the first and second exemplary embodiments, the microcontroller has been described as one example of controller 111. Using the programmable microcontroller as controller 111 allows processing contents to be changed by change of a program, which can increase a degree of freedom in design of controller 111. However, a configuration of controller 111 is not limited to the microcontroller, and may be implemented, for example, by hard logic such as an FPGA (Field-Programmable Gate Array) and an ASIC (Application Specific Integrated Circuit). Implementing controller 111 by the hard logic is effective for increase in processing speed. Controller 111 may be configured by one element, or may be physically configured by a plurality of elements. When controller 111 is configured by the plurality of elements, the respective controls described in the exemplary embodiments may be implemented by different elements. In this case, it can be considered that the plurality of elements configure one controller 111. Moreover, controller 111 and a member having another function may be configured by one element.

The present disclosure can be applied to a device that measures a biological signal such as an electrocardiogram, an electromyogram, and an electroencephalogram, to acquire the biological signal. Specifically, the present disclosure can be applied to an electrocardiograph, an electromyography, and the like.

What is claimed is:

1. A biological signal acquisition device comprising:
an electrode made up of a plurality of cell electrodes, and comes into contact with a biological body; and
a controller that acquires an electrical signal from the biological body through a pair of cell electrode groups made up of a part or all of the plurality of cell electrodes,
wherein the controller
determines a contact condition between the part or all of the plurality of cell electrodes and the biological body, based on a detection signal acquired by scanning the part or all of the plurality of cell electrodes, and
selects the cell electrodes making up the pair of cell electrode groups, based on the determined contact condition so that contact resistances between the cell electrode groups and the biological body are equal between the pair of cell electrode groups.

2. The biological signal acquisition device according to claim 1, wherein the controller determines the contact condition, based on a signal intensity of the detection signal.

3. The biological signal acquisition device according to claim 1, wherein the controller selects the cell electrodes making up the pair of cell electrode groups from the cell electrodes determined to be in contact with the biological body, based on the detection signal.

4. The biological signal acquisition device according to claim 3, wherein the controller selects the cell electrodes making up the pair of cell electrode groups so that a sum of a contact area between the cell electrodes making up one of the pair of the cell electrode groups, and the biological body is equal to a sum of a contact area between the cell electrodes making up the other of the pair of the cell electrode groups, and the biological body.

5. The biological signal acquisition device according to claim 3, wherein the controller selects the cell electrodes making up the pair of cell electrode groups so that numbers of the cell electrodes making up the respective cell electrode groups are equal between the pair of cell electrode groups.

6. The biological signal acquisition device according to claim 1, wherein the controller selects the cell electrodes making up the pair of cell electrode groups from the cell electrodes determined to be in contact with the biological body, based on the detection signal.

7. The biological signal acquisition device according to claim 6, wherein the controller selects the cell electrodes making up the pair of cell electrode groups so that a sum of a contact area between the cell electrodes making up one of the pair of the cell electrode groups, and the biological body is equal to a sum of a contact area between the cell electrodes making up the other of the pair of the cell electrode groups, and the biological body.

8. The biological signal acquisition device according to claim 6, wherein the controller selects the cell electrodes making up the pair of cell electrode groups so that numbers of the cell electrodes making up the respective cell electrode groups are equal between the pair of cell electrode groups.

9. The biological signal acquisition device according to claim 1, wherein
the controller selects a pair of candidate groups made up of a part or all of the plurality of cell electrodes,
one or more of the cell electrodes in at least one of the pair of candidate groups are opened so that contact resistances between the cell electrodes and the biological body are equal between the pair of candidate groups, and
at least one of the pair of cell electrode groups is made up of the cell electrodes not opened in the candidate group.

10. The biological signal acquisition device according to claim 1, wherein the controller obtains an electrocardiographic waveform based on the electrical signal.

11. The biological signal acquisition device according to claim 1, wherein
the controller selects a pair of candidate groups made up of a part or all of the cell electrodes making up the electrode, based on a differential signal intensity between the candidate groups, and
selects the cell electrodes making up the cell electrode groups corresponding to the respective candidate groups from the cell electrodes making up the respective candidate groups.

12. The biological signal acquisition device according to claim 1, wherein when the contact condition between any of the cell electrodes and the biological body changes, the controller again acquires the detection signal from the cell electrode, the contact condition of which has been changed, by again scanning the relevant cell electrode.

13. A method for acquiring a biological signal in which an electrode made up of a plurality of cell electrodes is brought into contact with a biological body to acquire an electrical signal from the biological body, the method comprising:
- acquiring a detection signal by scanning a part or all of the plurality of cell electrodes;
- determining a contact condition between the part or all of the plurality of cell electrodes and the biological body, based on the detection signal;
- deciding a pair of cell electrode groups from the plurality of cell electrodes, based on the determined contact condition;
- selecting the cell electrodes making up the pair of cell electrode groups so that contact resistances between the cell electrode groups and the biological body are equal between the pair of cell electrode groups in the decision of the pair of cell electrode groups; and
- acquiring the electrical signal from the pair of cell electrode groups.

* * * * *